(12) United States Patent
Jung et al.

(10) Patent No.: US 10,982,999 B2
(45) Date of Patent: Apr. 20, 2021

(54) SYSTEM AND METHOD FOR MEASURING ULTRAVIOLET RAY PROTECTION OF COSMETIC MATERIAL

(71) Applicant: Amorepacific Corporation, Seoul (KR)

(72) Inventors: Yu-Chul Jung, Yongin-si (KR); Hae-Kwang Lee, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 16/336,808

(22) PCT Filed: Sep. 26, 2017

(86) PCT No.: PCT/KR2017/010578
§ 371 (c)(1),
(2) Date: Mar. 26, 2019

(87) PCT Pub. No.: WO2018/062797
PCT Pub. Date: Apr. 5, 2018

(65) Prior Publication Data
US 2019/0242745 A1 Aug. 8, 2019

(30) Foreign Application Priority Data
Sep. 27, 2016 (KR) .......... 10-2016-0124226

(51) Int. Cl.
G01N 21/33 (2006.01)
G01J 1/42 (2006.01)
(Continued)

(52) U.S. Cl.
CPC ............ G01J 1/429 (2013.01); G01J 1/42 (2013.01); G01N 21/33 (2013.01); G01N 33/15 (2013.01); G01N 33/50 (2013.01)

(58) Field of Classification Search
CPC ............ G01J 1/429; G01J 1/42; G01N 21/33
See application file for complete search history.

(56) References Cited

U.S. PATENT DOCUMENTS

| 2010/0012850 A1 | 1/2010 | Miura et al. |
| 2012/0022472 A1* | 1/2012 | Miura ............... G01N 21/59 604/290 |

(Continued)

FOREIGN PATENT DOCUMENTS

| JP | 2008214465 A | 9/2008 |
| JP | 2016161534 A | 9/2016 |

(Continued)

OTHER PUBLICATIONS

Fuji Film; UVSCALE Visualizes UV light amount distribution by color density, Ultraviolet Light Amount Distribution Measurement Film, www.Sensorprod.com., Apr. 15, 2014 (Year: 2014).*

(Continued)

Primary Examiner — Hugh Maupin
(74) Attorney, Agent, or Firm — Cantor Colburn LLP

(57) ABSTRACT

A system and a method for measuring ultraviolet ray protection of a cosmetic material. In an embodiment, the system for measuring the ultraviolet ray protection of a cosmetic material includes: a light source for emitting light including ultraviolet bands; a transparent plate through which the lights emitted from the light source pass, and having one surface to which a cosmetic material to be tested is applied; a wavelength conversion film, which changes, to a predetermined size, the light, of an ultraviolet band, of the light having passed through the transparent plate and makes the same pass therethrough; and a photosensitive sheet, which accommodates the light having passed through the wavelength conversion film and has a photosensitive property for light of UVA and UVB bands among the ultraviolet bands.

8 Claims, 10 Drawing Sheets

(51) Int. Cl.
    *G01N 33/15*     (2006.01)
    *G01N 33/50*     (2006.01)

(56)     References Cited

U.S. PATENT DOCUMENTS

| | | | |
|---|---|---|---|
| 2013/0169951 A1* | 7/2013 | Miura | G01N 17/004 |
| 2014/0038305 A1* | 2/2014 | Sharavara | C09D 11/50 |
| | | | 436/164 |
| 2016/0035914 A1* | 2/2016 | Deliwala | H01L 31/103 |
| | | | 257/432 |

FOREIGN PATENT DOCUMENTS

| | | |
|---|---|---|
| KR | 1020090061007 A | 6/2009 |
| KR | 1020120054861 A | 5/2012 |
| KR | 1020130089433 A | 8/2013 |
| KR | 1020150064573 A | 6/2015 |
| KR | 1020150140955 A | 12/2015 |
| KR | 1020160004459 A | 1/2016 |
| WO | 2018062797 A1 | 4/2018 |

OTHER PUBLICATIONS

Korean Notice of Allowance dated Jun. 20, 2019, 3 pp.
International Search Report for International Application No. PCT/KR2017/010578, International Filing Date Sep. 26, 2017, dated Jan. 9, 2018, 4 pages.

\* cited by examiner

SYSTEM AND METHOD FOR MEASURING ULTRAVIOLET RAY PROTECTION OF COSMETIC MATERIAL

TECHNICAL FIELD

The present invention relates to a system and method for measuring ultraviolet ray protection of a cosmetic material and, more particularly, to a system and method for measuring ultraviolet ray protection of a cosmetic material, the system and method being able to measure the ultraviolet ray protection ability of a cosmetic material quickly with high reliability using a photosensitive sheet.

BACKGROUND ART

Cosmetic materials that are used for ultraviolet ray protection are used to block ultraviolet rays of the sunlight. These cosmetic materials have different ultraviolet ray protection, so various methods for accurately measuring the abilities have been used.

In the related art, the ultraviolet ray protection of cosmetic materials was measured through an in-vivo test. The ultraviolet ray protection was measured by measuring the ratio of a light amount causing an erythema after applying products to a light amount causing an erythema before applying the products through clinical tests. However, although accuracy is secured since the in-vivo test are performed actually on a person, but the test subject has to be exposed to ultraviolet rays, so there are inconvenience and danger. A method of comparing a gene expression amounts in skin cells due to the sunlight is disclosed in KR10-2015-0064573 A, but this also includes the problem that a test subject has to be exposed to ultraviolet rays.

Meanwhile, the ultraviolet ray protection of cosmetic materials was measured through an in-vitro test in some cases. In detail, a method of measuring a transmission property by applying a cosmetic material to a plate was selected in some cases. However, in the in-vitro test, the ultraviolet ray blocking agent decreases in activity as it receives ultraviolet rays, so a correction reflecting this problem is required. Further, a plate cannot induce an erythema, so a weight is required for a wavelength causing an erythema in calculation. Accordingly, various mathematical corrections, for example, applying a weight, are used, so there is a problem that there is a large error or deviation in the resultant value. Further, the amounts of cosmetic materials applied to a plate are not uniform, so there is a problem that a large error is generated.

SUMMARY OF INVENTION

Technical Problem

The present invention has been made in an effort to solve the problems, and an object of the present invention is to provide a system and method for measuring ultraviolet ray protection of a cosmetic material, the system and method being able to obtain a result similar to that in an in-vivo test.

Another object of the present invention is to provide a system and method for measuring ultraviolet ray protection of a cosmetic material, the system and method securing accuracy with a small error or deviation by minimizing mathematical calculations by applying the same actual examination time.

Another object of the present invention is to provide a system and method for measuring ultraviolet ray protection of a cosmetic material, the system and method being quickly performed by applying an in-vitro test, reducing a deviation in application of a product, and decreasing danger on a test subject.

Solution to Problem

A system and a method for measuring ultraviolet ray protection of a cosmetic material according to an embodiment of the present invention includes: a light source for emitting light including ultraviolet bands; a transparent plate through which the light emitted from the light source passes and having one surface to which a cosmetic material to be tested is applied; a wavelength conversion film which changes, to a predetermined size, the light with an ultraviolet band of the light having passed through the transparent plate and makes the same pass therethrough; and a photosensitive sheet, which accommodates the light having passed through the wavelength conversion film and has a photosensitive property for light of UVA and UVB bands among the ultraviolet bands.

The system may further include an ultraviolet ray protection calculator that calculates the ultraviolet ray protection of a cosmetic material in accordance with reaction time at which the photosensitive sheet reacts for predetermined light intensity, or calculates the ultraviolet ray protection of a cosmetic material in accordance with reaction light intensity at which the photosensitive sheet reacts for predetermined reaction time.

The ultraviolet ray protection calculator may calculate an ultraviolet ray protection index through the ratio of reaction time or light intensity for a photosensitive sheet of a transparent plate having a cosmetic material to be tested applied to a side, to reaction time or reaction light intensity for a photosensitive sheet of a transparent plate without a cosmetic material applied.

The system may further include: a database storing one or more of reaction time information of a photosensitive sheet for predetermined light intensity corresponding to an ultraviolet ray protection index and reaction light intensity information of a photosensitive sheet for predetermined reaction time; and an ultraviolet ray protection calculator connected to the database and calculating an ultraviolet ray protection index corresponding to reaction time or reaction light intensity for a photosensitive sheet of a cosmetic material.

The photosensitive sheet may not have a photosensitive property for bands of 380 nm or more.

The photosensitive sheet may have a photosensitive property for UVA II and UVB bands.

The photosensitive sheet may have a photosensitive property for a UVB band.

A method of measuring ultraviolet ray protection of a cosmetic material according to an embodiment of the present invention includes: a step of measuring first reaction time by irradiating light from a light source, which has predetermined light intensity including ultraviolet ray bands, to a photosensitive sheet having a photosensitive property for light of UVA and UVB bands of the ultraviolet ray bands through a wavelength conversion film that changes light of ultraviolet ray bands into predetermined sizes; a step of disposing a transparent plate having a cosmetic material to be tested applied on a side between the light source and the wavelength conversion film; a step of measuring second reaction time by irradiating light from the light source to the photosensitive sheet through the transparent plate and the wavelength conversion film; and a step of calculating ultraviolet ray protection index in accordance with the ratio of the second reaction time to the first reaction time.

A method of measuring ultraviolet ray protection of a cosmetic material according to another embodiment of the present invention includes: a step of measuring first light intensity for predetermined reaction time by irradiating light from a light source, which has predetermined light intensity including ultraviolet ray bands, to a photosensitive sheet having a photosensitive property for light of UVA and UVB bands of the ultraviolet ray bands through a wavelength conversion film that changes light of ultraviolet ray bands into predetermined sizes; a step of disposing a transparent plate having a cosmetic material to be tested applied on a side between the light source and the wavelength conversion film; a step of measuring second light intensity for predetermined reaction time by irradiating light to a photosensitive sheet through the transparent plate and the wavelength conversion film; and a step of calculating an ultraviolet ray protection index in accordance with the ratio of the second light intensity to the first light intensity.

A method of measuring ultraviolet ray protection of a cosmetic material according to another embodiment of the present invention includes: a step of measuring reaction time or light intensity by irradiating light from a light source, which includes ultraviolet ray bands, to a photosensitive sheet having a photosensitive property for light of UVA and UVB bands of the ultraviolet ray bands through a transparent plate having a cosmetic material to be tested applied on a side and a wavelength conversion film that changes light of ultraviolet ray bands into predetermined sizes; and a step of calculating an ultraviolet ray protection index of the cosmetic material using one or more of reaction time information of a photosensitive sheet for predetermined light intensity corresponding to an ultraviolet ray protection index and reaction light intensity information of the photosensitive sheet for predetermined reaction time, in which the information is stored in advance.

Advantageous Effects of Invention

According to an embodiment of the present invention, a system and method for measuring ultraviolet ray protection of a cosmetic material that can obtain a result similar to an in-vivo test by applying a wavelength of an erythema reaction band of an actual skin can be provided.

Further, there can be provided a system and method for measuring an ultraviolet ray protection of a cosmetic material, the system and method securing accuracy with a small error or deviation by minimizing mathematical calculations by applying the same actual radiation time.

Further, there can be provided a system and method for measuring an ultraviolet ray protection of a cosmetic material, the system and method being quickly performed by applying an in-vitro test, reducing a deviation in application of a product, and decreasing danger on a test subject.

Further, there can be provided a system and method for measuring an ultraviolet ray protection of a cosmetic material, the system and method being able to minimize an error due to application of a cosmetic material as the reaction time of a photosensitive sheet or light intensity is measured.

DESCRIPTION OF EMBODIMENTS

Figure 1:
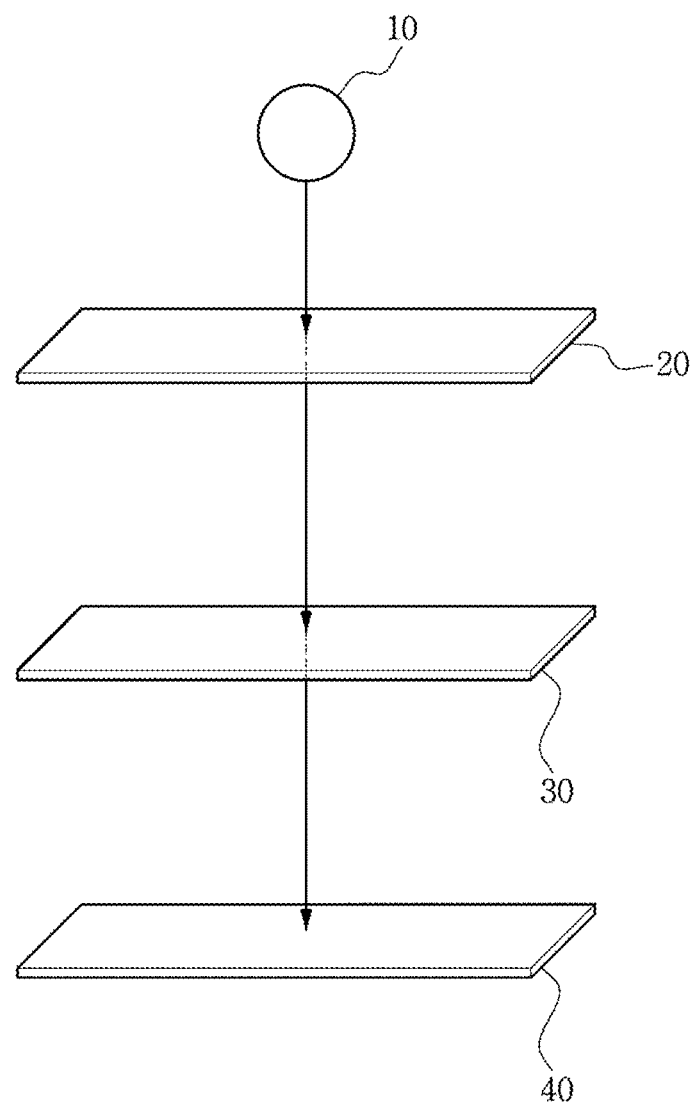
FIG. 1 is a view schematically showing a system for measuring ultraviolet ray protection of a cosmetic material according to an embodiment of the present invention.

The present invention may be modified in various ways and implemented by various exemplary embodiments, so specific exemplary embodiments are shown in the drawings and will be described in detail. However, it is to be understood that the present invention is not limited to the specific exemplary embodiments, but includes all modifications, equivalents, and substitutions included in the spirit and the scope of the present invention. When functions and configurations of components well known in the art may make the gist of the present invention unclear, a detailed description of the components will be omitted in the following description of embodiments.

In the embodiments, '~ module' or '~ unit' performs at least one function or operation and can be implemented by hardware or software or a combination of hardware and software. Further, a plurality of 'modules' or a plurality of 'units' can be integrated in at least one module and can be implemented in at least one processor (not shown) except for 'modules' or 'units' required to be implemented by specific hardware.

Hereinafter, embodiments of the present invention are described in detail with reference to accompanying drawings, and in the following description of the accompanying drawings, like reference numerals are given to like components and repetitive description is omitted.

FIG. 1 is a view schematically showing a system for measuring ultraviolet ray protection of a cosmetic material according to an embodiment of the present invention.

Referring to FIG. 1, a system for measuring ultraviolet ray protection of a cosmetic material according to an embodiment of the present invention includes: a light source 10 for emitting light including ultraviolet bands; a transparent plate 20 through which the light emitted from the light source 10 passes and having one surface to which a cosmetic material to be tested is applied; a wavelength conversion film 30, which changes, to a predetermined size, the light with an ultraviolet band of the light having passed through the transparent plate 20 and makes the same pass therethrough; and a photosensitive sheet 40, which accommodates the light having passed through the wavelength conversion film 30 and has a photosensitive property for light of UVA (UVA I, II) and UVB bands among the ultraviolet bands.

The system for measuring ultraviolet ray protection according to an embodiment of the present invention is formed to induce an erythema reaction in a similar way to the structure of an in-vivo test.

To this end, the system includes the light source 10 that corresponds to the sunlight or artificial light, and the wavelength conversion film 30 and the photosensitive sheet 40 that induce a reaction similar to an erythema reaction to correspond to a skin. Further, the transparent plate 20 is disposed between the light source 10 and the wavelength conversion film 30 to correspond to the position of a cosmetic material that is applied to a skin such that the cosmetic material is applied to any one side thereof.

The transparent plate 20, according to an embodiment, may be a PMMA (poly(methyl methacrylate) plate, but is not limited thereto, and various plates that do not influence the wavelengths and intensity of ultraviolet ray bands can be used.

The light source 10 is a part emitting light including ultraviolet ray bands, and the light emitted from the light source 10 reaches the photosensitive sheet 40 through the wavelength conversion film 30 to have a reaction band similar to an effective spectrum causing an erythema.

Figure 2:
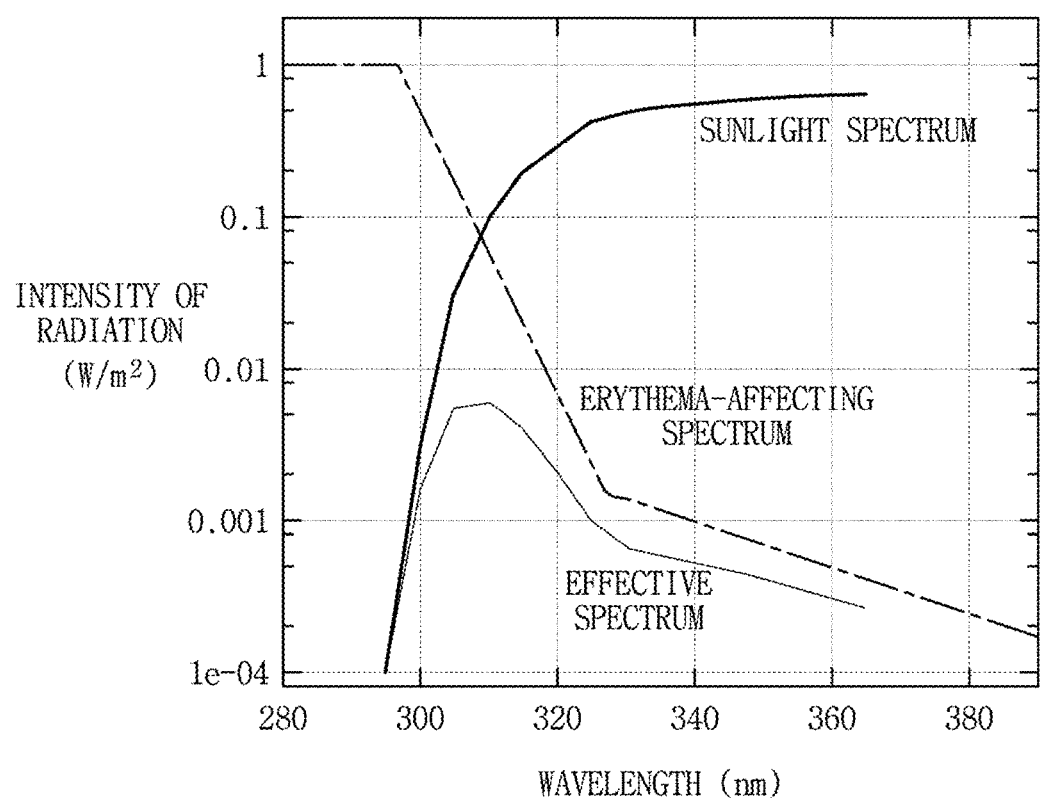
FIG. 2 is a graph comparing a sunlight spectrum, an erythema-affecting spectrum, and an effective spectrum that affects an erythema.

In more detail, FIG. 2 is a graph comparing a sunlight spectrum, an erythema-affecting spectrum, and an effective spectrum that influences an erythema.

Referring to FIG. 2, a sunlight spectrum has a feature that it gradually increases at a wavelength band of about 200 nm or more. An erythema-affecting spectrum that causes an erythema on a skin has a tendency that is has the largest effect at 280 nm, gradually decreases and rapidly decreases at about 320 nm, and smoothly increases after about 320 nm. Accordingly, considering that the sunlight spectrum has ultraviolet rays of about 290 nm or more, the effective spectrum that actually causes an erythema in the sunlight spectrum has a tendency that it rapidly increases at about 290 nm, reaches the peak at about 310 nm, and then gradually decreases.

When ultraviolet ray protection test is performed by an in-vitro test, the effect by the effective spectrum that actually causes an erythema in the sunlight should be tested, so a photosensitive sheet having a reaction spectrum like a skin on which an erythema is caused should be used.

To this end, according to an embodiment of the present invention, the sunlight or a similar light source is used as the light source, and a structure having a reaction spectrum the same as the effective spectrum that causes an erythema is used.

Figure 3A:
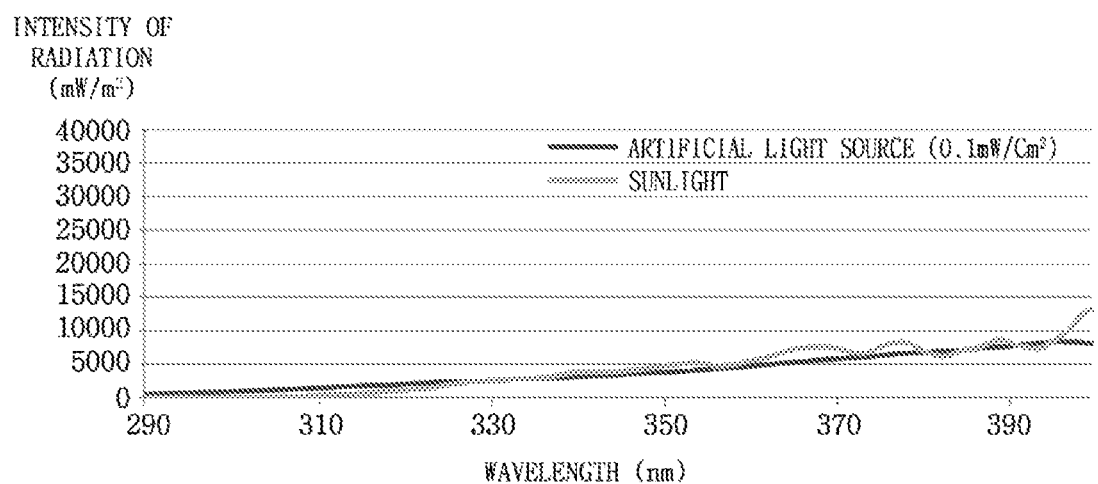
FIG. 3A is a graph comparing intensity according to wavelengths of the sunlight and light emitted from a light source in the system for measuring ultraviolet ray protection of a cosmetic material according to an embodiment of the present invention.
Figure 3B:
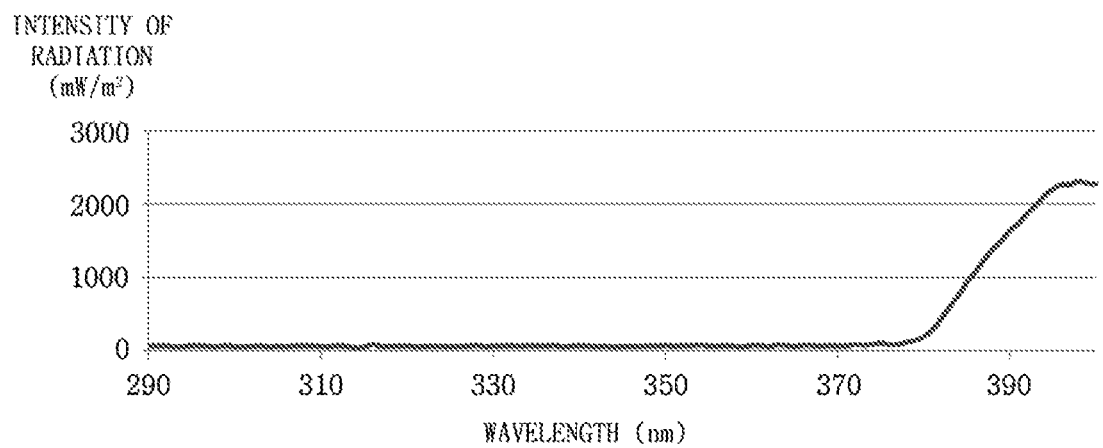
FIG. 3B is a graph showing the intensity according to a wavelength after emitted light passes through a wavelength conversion film.
Figure 3C:
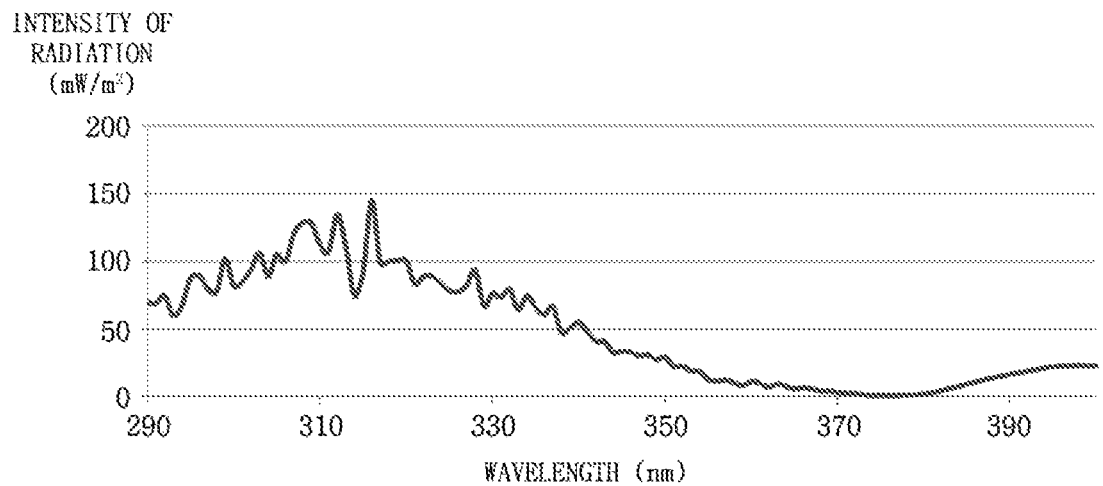
FIG. 3C is a graph showing reaction intensity according to a wavelength that reacts to a photosensitive sheet.

FIG. 3A is a graph comparing intensity according to wavelengths of the sunlight and light emitted from a light source in the system for measuring ultraviolet ray protection of a cosmetic material according to an embodiment of the present invention, FIG. 3B is a graph showing the intensity according to a wavelength after emitted light passes through a wavelength conversion film, and FIG. 3C is a graph showing response intensity according to a wavelength that reacts to a photosensitive sheet.

Referring to FIG. 3, according to an embodiment of the present invention, the light source 10 includes light of ultraviolet ray bands, and as in FIG. 3A, a light source having a spectrum that gradually increases from a 290 nm band may be used. Further, it should be understood that the sunlight itself can be used as the light source 10.

According to an embodiment, for the light source 10, multiport 601 or 1-port by Solar Light (U.S.) may be used as an artificial light source.

Cosmetic materials having an ultraviolet ray protection function had a tendency that the activity decreases as time passes. To reflect this problem, it is required to examine in advance the activity reduction tendency according to time of cosmetic materials in an in-vitro test, and various mathematic corrections had to be reflected to reflect this fact. However, according to an embodiment of the present invention, as the light source 10, as the sunlight itself or a light source having a wavelength spectrum similar to the sunlight is used, there is no need for such investigation and mathematic corrections. Accordingly, the test time can be reduced, and there is no large deviation in the result because there is no mathematic correction.

Further, since the actual sunlight or a light source having wavelength spectrum distribution similar to the sunlight is used, a reaction can be derived at the same time as the actual examination time in an in-vivo test. Since mathematic calculations for correction can be reduced, it is possible to further decrease a deviation and errors in the result.

The wavelength conversion sheet 30 and the photosensitive sheet 40 are structures that correspond to a skin, and the photosensitive sheet 40 is given a reaction band similar to the effective spectrum that causes an erythema.

Ultraviolet rays, in broad meaning, are classified into UVC (about 200 to 290 nm), UVB (about 290 to 320 nm), UVA-II (about 320 to 340 nm), and UVA-I (about 340 to 400 nm).

The wavelength conversion sheet 30, as shown in FIG. 3B, converts a wavelength of an ultraviolet ray band into a predetermined size and then transmits it.

Though not necessarily limited thereto, according to an embodiment of the present invention, the effective spectrum of an erythema is close to 0 at about 380 nm or less, so wavelengths 380 nm or greater do not affect the generation of an erythema even if they exist. According to an embodiment, the wavelength conversion sheet 30 may be formed to convert the wavelengths of 380 nm or less into predetermined sizes.

In the embodiment of FIG. 3B, wavelengths are converted to have predetermined intensity. The present invention is not necessarily limited thereto, and wavelengths can be converted into various sizes such that the sizes are uniformly decreased. According to an embodiment, an ultraviolet ray-blocking film may be used as the wavelength conversion sheet 30.

In order to accurately measure the ultraviolet ray protection, the reaction band of the photosensitive sheet 40 to which light is finally irradiated should have a band similar to the effective spectrum of FIG. 2.

Therefore, according to an embodiment of the present invention, the reaction band of the photosensitive sheet 40 has to have a photosensitive property for light of UVA (about 320 to 400 nm) and UVB (about 290 to 320 nm) bands, in which an effective spectrum for an erythema of wavelengths of band passing through the wavelength conversion sheet 30 is distributed.

Further, according to an embodiment of the present invention, the photosensitive sheet 40 may not have a photosensitive property in bands of about 380 nm or greater. Referring to the effective spectrum of FIG. 2, wavelengths of 380 nm or greater do not affect the generation of an erythema even if they exist, so a photosensitive property may not be given to bands of about 380 nm or greater so as not to affect the photosensitive property of the photosensitive sheet 40.

Figure 4A:
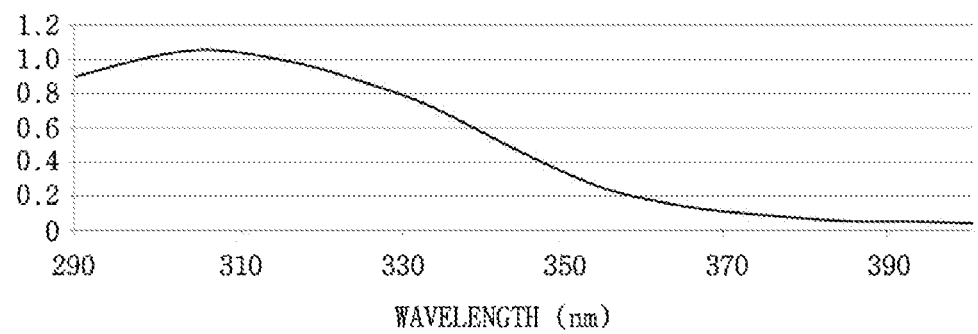
FIG. 4A is a graph showing a reaction band of a photosensitive sheet according to an embodiment of the present invention and FIG. 4B is a graph showing reaction intensity according to a wavelength of a photosensitive sheet when there is no wavelength conversion film.

FIG. 4A is a graph showing a reaction band of the photosensitive sheet 40 according to an embodiment. The embodiment of FIG. 4A is an embodiment where the photosensitive sheet 40 has a photosensitive property for light of UVA (about 320 to 400 nm) and UVB (about 290 to 320 nm) bands and does not have a photosensitive property at about 380 nm or less.

When such photosensitive sheet 40 is applied, the photosensitive sheet 40 has a reaction spectrum at the wavelength spectrum shown in FIG. 3C. Further, it can be seen that the reaction spectrum of FIG. 3C is similar to the effective spectrum causing an erythema of FIG. 2.

According to another embodiment of the present invention, most of the effective spectrum that affects an erythema is distributed in UVA II and UVB regions. Therefore, according to an embodiment, the photosensitive sheet 40 may have a photosensitive property for the UVA (about 320 to 400 nm) and UVB (about 290 to 320 nm) bands.

According to another embodiment of the present invention, the effective spectrum that affects an erythema is the highest when receiving an ultraviolet ray of the UVB region, so the photosensitive sheet 40 may have a photosensitive property for the UVB (about 290 to 320 nm) band.

Figure 4B:
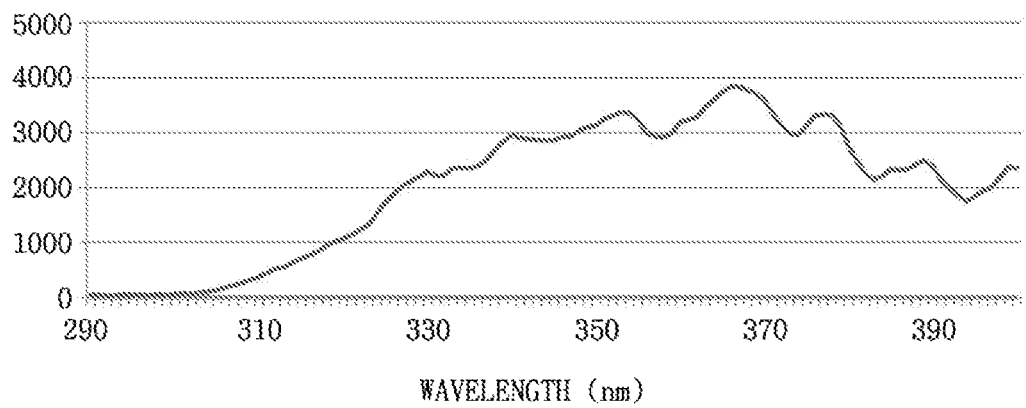

Meanwhile, FIG. 4B shows a reaction spectrum for a light source of the photosensitive sheet 40 having the reaction band of FIG. 4A when the wavelength conversion sheet 30 is not applied.

In other words, when the artificial light source or the sunlight source of FIG. 3A is irradiated directly to the photosensitive sheet 40 having the reaction band of FIG. 4A, the reaction spectrum is shown as in FIG. 4B. The reaction spectrum is very different from the effective spectrum for an erythema.

The applied artificial light source or sunlight source has a spectrum where the intensity of a wavelength gradually increases as the wavelength increases, so the photosensitive sheet 40 has a reaction spectrum having a very different form from the effective spectrum for an erythema, even if it has the reaction band shown in FIG. 4A.

Therefore, according to an embodiment of the present invention, it is possible to achieve a reaction spectrum similar to the effective spectrum that causes an erythema by combining the wavelength conversion sheet 30 and the photosensitive sheet 40. That is, it is possible to derive the same result as an in-vivo test even without performing an in-vivo test.

Meanwhile, whether the photosensitive sheet 40 reacts or not can be confirmed through a change in color of the region, to which a light source is irradiated, of the photosensitive sheet 40. Though not necessarily limited thereto, it is possible to analyze the color of a reaction region of the photosensitive sheet 40 through an image processor including an image device or an image sensor, and for example, it is possible to determine whether it reacts or not by sensing whether pixels over a predetermined ratio of a predetermined region is changed. Further, it should be understood that a test operator checks a change in the reaction region of the photosensitive sheet 40, inputs the point of time of reaction or the light intensity at reaction to an input device such that it is transmitted to an ultraviolet ray protection calculator.

When transmittance is measured in an in-vitro test, the transmittance changes in accordance with application of cosmetic materials, so errors are generated. However, according to an embodiment of the present invention, since whether a photosensitive sheet reacts or not is determined throughout the photosensitive sheet, it is not sensitively affected by the application of cosmetic materials, so the errors can be minimized. It is possible to more accurately measure ultraviolet ray protection.

According to an embodiment of the present invention, it is possible to measure ultraviolet ray protection using the system for measuring ultraviolet ray protection of a cosmetic material described above.

According to an embodiment, the system can calculate ultraviolet ray protection according to a change of the photosensitive sheet 40.

Alternatively, it may be possible to calculate ultraviolet ray protection of a cosmetic material according to reaction time at which the photosensitive sheet 40 reacts, for predetermined light intensity.

The ultraviolet ray protection can be measured in a way of calculating an ultraviolet ray protection index such as an SPF (Sun Protection Factor) or a PFA (Protection factor of UVA)

For example, the SPF is measured by the following [Formula 1].

$$SPF = \frac{MEDp}{MEDu} = \frac{\text{Light amount causing erythema after cosmetic material is applied}}{\text{Light amount causing erythema before cosmetic material is applied}} \quad \text{[Formula 1]}$$

Further, the light amount can be expressed as in the following [Formula 2].

$$\text{Light amount} = \text{Light intensity} \times \text{Light irradiation time} \quad \text{[Formula 2]}$$

Therefore, according to an embodiment of the present invention, the system can measure light intensity or reaction time where the photosensitive sheet 40 reacts before a cosmetic material is applied to the transparent plate 20, and can measure light intensity or reaction time where the photosensitive sheet 40 reacts after the cosmetic material is applied to the transparent plate 20.

Then, if the light intensity of the light source 10 was constant at a predetermined intensity, it is possible to calculate an SPF ultraviolet ray protection index through the ratio of the reaction times before and after the cosmetic material is applied. Alternatively, if the reaction time is constant, it is possible to calculate an SPF ultraviolet ray protection index through an ultraviolet ray protection index from the ratio of the light intensity where the photosensitive sheet 40 reacts.

Alternatively, if there is information of light intensity or reaction time or both of them where the photosensitive sheet 40 reacts for an ultraviolet ray protection index known or stored in advance, it may be possible to calculate the ultraviolet ray protection index corresponding to the information of the reaction time or the light intensity of the photosensitive sheet 40 measured after applying a cosmetic material to the transparent plate 20.

Further, even if an ultraviolet ray protection index is not calculated, if the ultraviolet ray protection indexes of a plurality of cosmetic materials are to be compared, it may be possible to compare ultraviolet ray protection indexes of cosmetic materials by applying the cosmetic materials to a plurality of transparent plates 20 and then comparing the reaction time or light intensity of the photosensitive sheets 40.

Meanwhile, the ultraviolet ray protection indexes may be measured by a test operator using the system according to an embodiment of the present invention, and it may be possible to further provide a separate ultraviolet ray protection index calculator 50, which calculates an ultraviolet ray protection index in accordance with a change in the photosensitive sheet 40, to the system to calculate an ultraviolet ray protection index.

Figure 5:
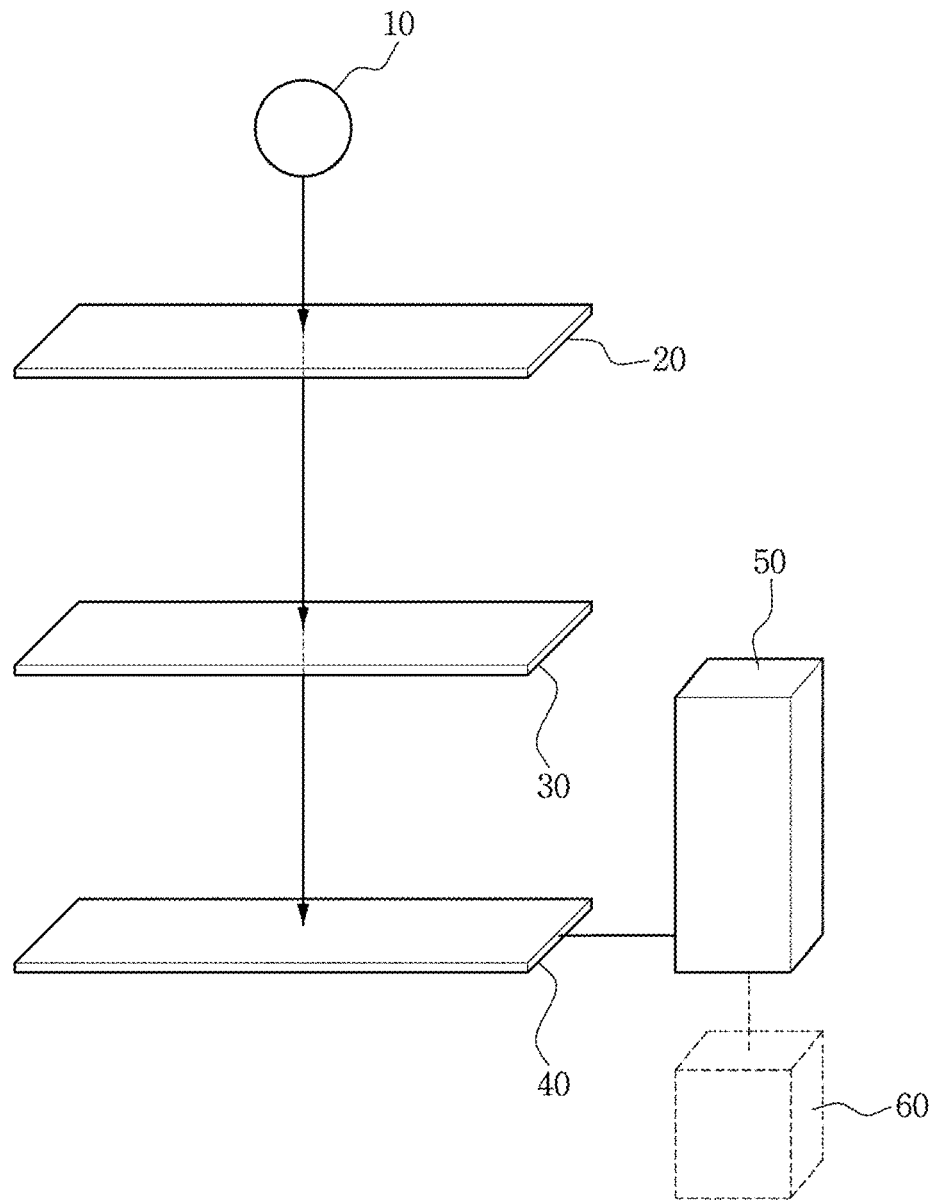
FIG. 5 is a view schematically showing a system for measuring ultraviolet ray protection of a cosmetic material according to another embodiment of the present invention.

FIG. 5 is a view schematically showing a system for measuring ultraviolet ray protection of a cosmetic material according to another embodiment of the present invention.

In detail, the ultraviolet ray protection index calculator 50 may calculate ultraviolet ray protection of a cosmetic material according to reaction time at which the photosensitive sheet 40 reacts, for predetermined light intensity.

Alternatively, the ultraviolet ray protection index calculator 50 may calculate ultraviolet ray protection of a cosmetic material in accordance with light intensity where the photosensitive sheet 40 reacts, for predetermined reaction time.

According to an embodiment of the present invention, it is possible to compare or analyze ultraviolet ray protection of one or more cosmetic materials in accordance with reaction time or light intensity where the photosensitive sheet 40 reacts.

Further, the ultraviolet ray protection index calculator 50 can calculate an ultraviolet ray protection index through the ratio of reaction time or reaction light intensity values of the transparent plate 20 with a cosmetic material applied thereon for the photosensitive sheet, to reaction time or reaction light intensity of the transparent plate 20 without the cosmetic material to be tested applied thereon for the photosensitive sheet.

As described above, if a test is performed with light intensity maintained at a predetermined value, it is possible to calculate an ultraviolet ray protection index with the ratio of reaction time before and after a cosmetic material is applied, and if reaction time was constant as a predetermined value, it is possible to calculate an ultraviolet ray protection index with the ratio of reaction light intensity before and after the cosmetic material is applied.

Meanwhile, the system may further include a database 60 that is connected to the ultraviolet ray protection index calculator 50 and stores one or more of reaction time information of the photosensitive sheet 40 for predetermined light intensity corresponding to an ultraviolet ray protection index and reaction light intensity information of the photosensitive sheet 40 for predetermined reaction time.

Accordingly, the ultraviolet ray protection index calculator 50 may calculate an ultraviolet ray protection index corresponding to reaction time or reaction light intensity by measuring only the reaction time or the reaction light intensity where the photosensitive sheet reacts after a cosmetic material is applied, without measuring reaction time or light intensity of the photosensitive sheet before the cosmetic material is applied.

According to an embodiment of the present invention, it is possible to measure ultraviolet ray protection using the system for measuring ultraviolet ray protection of a cosmetic material described above, and the contents about the system can be applied to the method of measuring ultraviolet ray protection.

Figure 6:
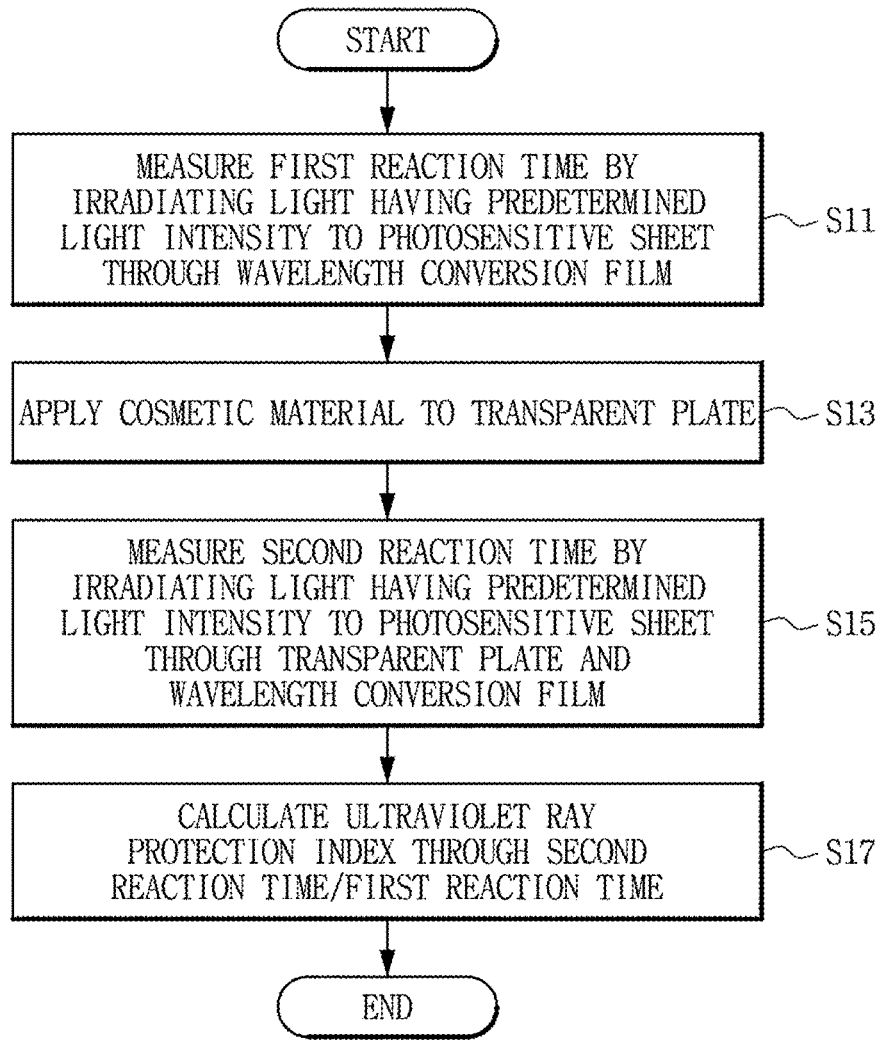
FIG. 6 is a flowchart schematically showing a method for measuring ultraviolet ray protection of a cosmetic material according to an embodiment of the present invention.

FIG. 6 is a flowchart schematically showing a method for measuring ultraviolet ray protection of a cosmetic material according to an embodiment of the present invention.

Referring to FIG. 6, a method for measuring ultraviolet ray protection of a cosmetic material according to another embodiment of the present invention includes a step (S11) of measuring first reaction time by irradiating light from a light source, which has predetermined light intensity including ultraviolet ray bands, to a photosensitive sheet having a photosensitive property for light of UVA and UVB bands of the ultraviolet ray bands through a wavelength conversion film that changes light of ultraviolet ray bands into predetermined sizes.

Then, the method includes a step (S13) of disposing a transparent plate having a cosmetic material to be tested applied on a side between the light source and the wavelength conversion film. When a plurality of cosmetic materials is used, the cosmetic materials can be applied by a predetermined amount to predetermined reaction regions on transparent plates.

Further, the method includes a step (S15) of measuring second reaction time by irradiating light from the light source to the photosensitive sheet through the transparent plate and the wavelength conversion film 30.

Further, the method includes a step (S17) of calculating ultraviolet ray protection index in accordance with the ratio of the second reaction time to the first reaction time. In this embodiment, the light source in the step (S11) and the step (S15) is given a predetermined light intensity, so an ultraviolet ray protection index can be calculated from the ratio of reaction time.

Figure 7:
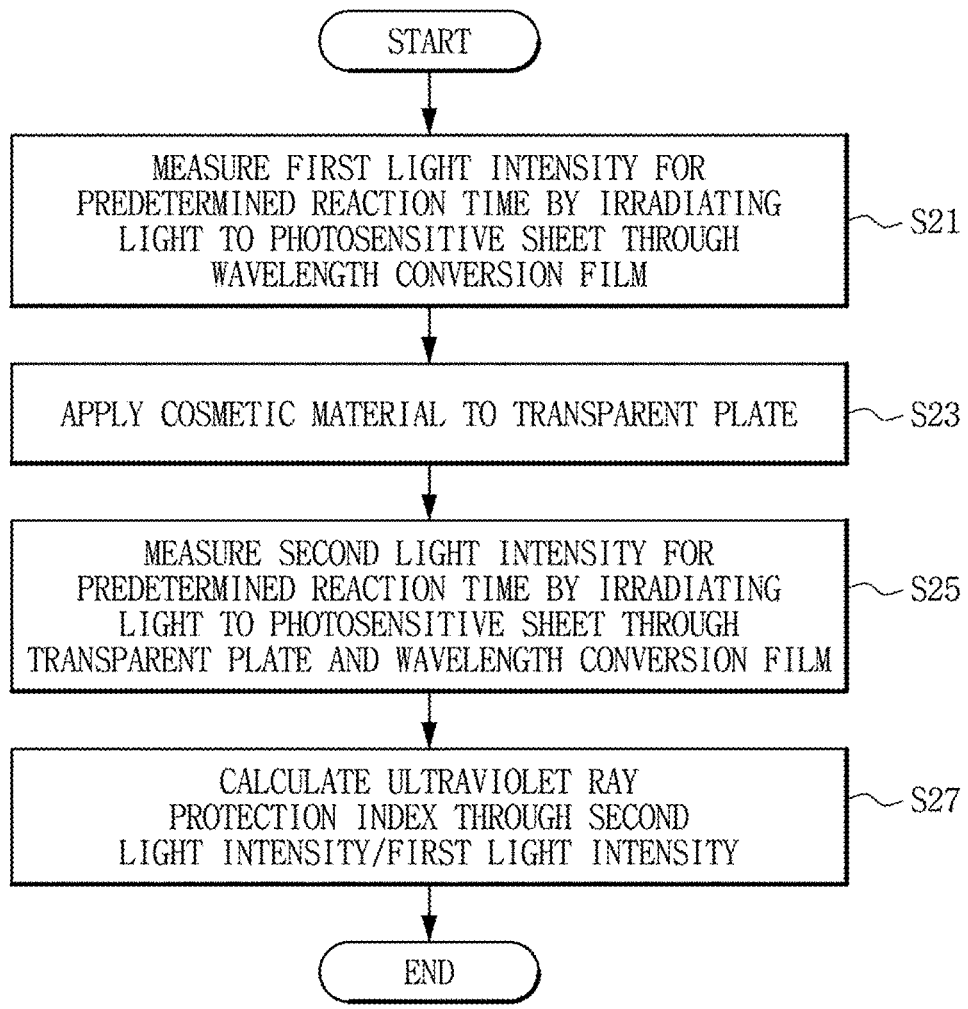
FIG. 7 is a flowchart schematically showing a method for measuring ultraviolet ray protection of a cosmetic material according to another embodiment of the present invention.

FIG. 7 is a flowchart schematically showing a method for measuring ultraviolet ray protection of a cosmetic material according to another embodiment of the present invention.

Referring to FIG. 7, a method for measuring ultraviolet ray protection of a cosmetic material according to another embodiment of the present invention includes a step (S21) of measuring first light intensity for predetermined reaction time by irradiating light from a light source, which has predetermined light intensity including ultraviolet ray bands, to a photosensitive sheet having a photosensitive property for light of UVA and UVB bands of the ultraviolet ray bands through a wavelength conversion film that changes light of ultraviolet ray bands into predetermined sizes.

Then, the method includes a step (S23) of disposing a transparent plate having a cosmetic material to be tested applied on a side between the light source and the wavelength conversion film.

Further, the method includes a step (S25) of measuring second light intensity for predetermined reaction time by irradiating light to a photosensitive sheet through the transparent plate and the wavelength conversion film and a step (S27) of calculating an ultraviolet ray protection index in accordance with the ratio of the second light intensity to the first light intensity.

In the embodiment of FIG. 7, the reaction time is controlled at a predetermined level in the step (S21) and the step (S25), so it is possible to calculate an ultraviolet ray protection index by measuring light intensity where a photosensitive sheet reacts.

Figure 8:
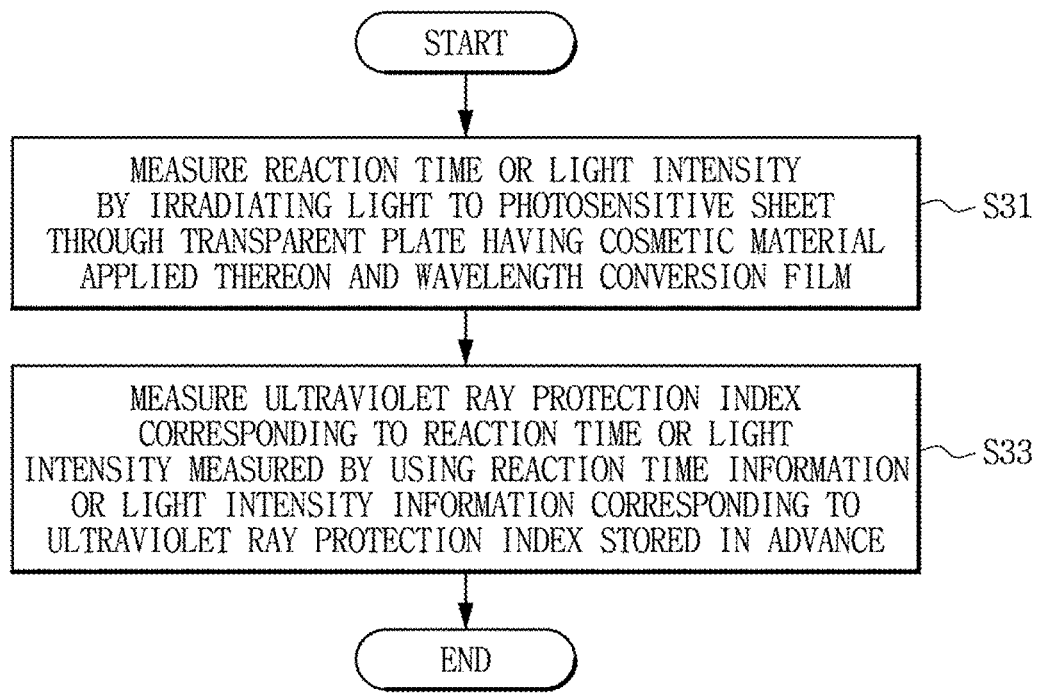
FIG. 8 is a flowchart schematically showing a method for measuring ultraviolet ray protection of a cosmetic material according to yet another embodiment of the present invention.

FIG. 8 is a flowchart schematically showing a method for measuring ultraviolet ray protection of a cosmetic material according to another embodiment of the present invention.

Referring to FIG. 8, a method for measuring ultraviolet ray protection of a cosmetic material according to another embodiment of the present invention includes a step (S31) of measuring reaction time or light intensity by irradiating light from a light source, which includes ultraviolet ray bands, to a photosensitive sheet having a photosensitive property for light of UVA and UVB bands of the ultraviolet ray bands through a transparent plate having a cosmetic material to be tested applied on a side and a wavelength conversion film that changes light of ultraviolet ray bands into predetermined sizes.

Further, the method includes a step (S33) of calculating an ultraviolet ray protection index of the cosmetic material using one or more of reaction time information of a photosensitive sheet for predetermined light intensity corresponding to an ultraviolet ray protection index and reaction light intensity information of the photosensitive sheet for predetermined reaction time, in which the information is stored in advance.

In this case, a process of measuring reaction of a photosensitive sheet before a cosmetic material is applied is not required, so it is possible to calculate an ultraviolet ray protection index within shorter time.

Embodiment 1

1-port by Solar Light (U.S.) was used as a light source, and UV-scale H by Fuji Film in Japan was used as a photosensitive sheet. Further, a PMMA plate (HD6 by Halioplate, France) was used at a transparent plate.

A change in the photosensitive sheet according to time was examined by irradiating light at constant light intensity using a first cosmetic material of which the SPF ultraviolet ray protection index was measured as SPF 50 to 55 and a second cosmetic material of which the ultraviolet ray protection index was measured as SPF 70 to 75 in an in-vivo test.

Further, the first and second cosmetic materials were applied to a 5×5 cm region on the transparent plate by the same amount of 2.0 mg/cm$^2$.

Figure 9A:
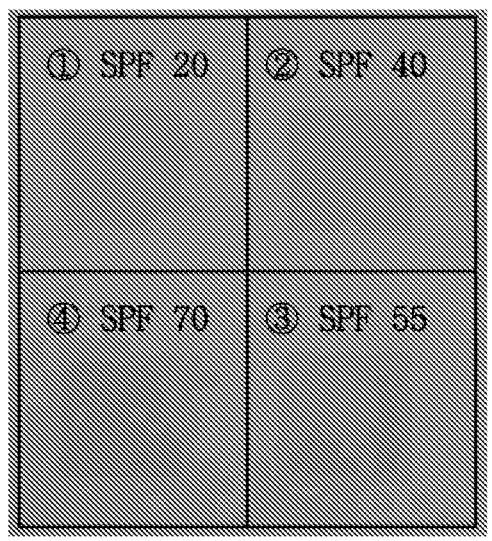
FIGS. 9A and B are pictures showing a change in a photosensitive sheet according to time of two kinds of cosmetic materials measured in accordance with an embodiment of the present invention.
Figure 9B:
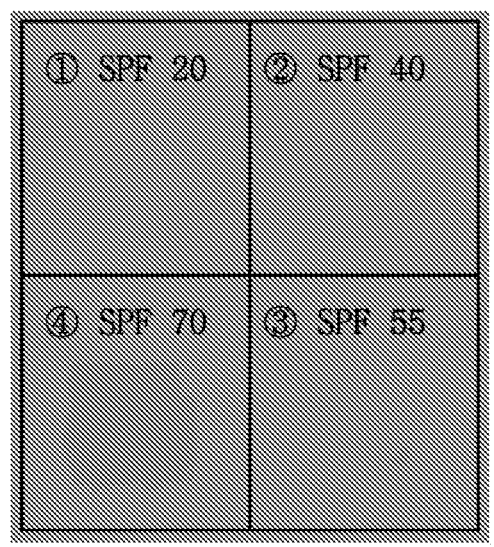

FIG. 9A is a picture showing a change of a photosensitive sheet according to time for the first cosmetic material and FIG. 9B is a picture showing a change of the photosensitive sheet according to time for the second cosmetic material.

Data stored in advance were used, the picture ① is a picture of time corresponding to an SPF index 20, the picture ② is a picture of time corresponding to an SPF index 40, the picture ③ is a picture of time corresponding to an SPF index 55, and the picture ④ is a picture of time corresponding to an SPF index 70.

In the embodiment of FIGS. 9A and 9B, a rectangular reaction region is shown on the photosensitive sheet, so the point of time when a complete rectangle is shown is the reaction time of the photosensitive sheet.

As a result, referring to FIG. 9A, the first cosmetic material showed a complete rectangle first in the picture ③, thus it can be seen that the ultraviolet ray index of the first cosmetic material is about SFP 55.

Further, referring to FIG. 9B, the second cosmetic material showed a complete rectangle first in the picture ④, thus it can be seen that the ultraviolet ray index of the second cosmetic material is about SFP 70.

As compared with the result of an in-vivo test, it can be seen that the same ultraviolet ray protection indexes are obtained because the first cosmetic showed SPF 50 to 55 as the result of the in-vivo test and about SFP 55 was measured in an embodiment of the present invention.

Further, the second cosmetic showed SPF 70 to 75 as the result of the in-vivo test and about SPF 70 was measured in an embodiment of the present invention, so it can be seen that the same ultraviolet ray indexes can be obtained.

That is, according to an embodiment of the present invention, it can be seen that an accurate result at the same level as in an in-vivo test can be obtained when an in-vitro test is even applied.

Embodiment 2

Multiport 601 by Solar Light (U.S.) was used as a light source, and UV-scale H by Fuji Film in Japan was used as a photosensitive sheet. Further, a PMMA plate (HD6 by Halioplate in France) was used at a transparent plate.

A third cosmetic material was applied at 2.0 mg/cm$^2$ on the transparent plate. Further, light having a wavelength spectrum similar to the sunlight was irradiated to the third cosmetic material of which the SPF ultraviolet ray protection index was measured as SPF 28 in an in-vivo test while the light intensity was gradually increased.

Figure 10:
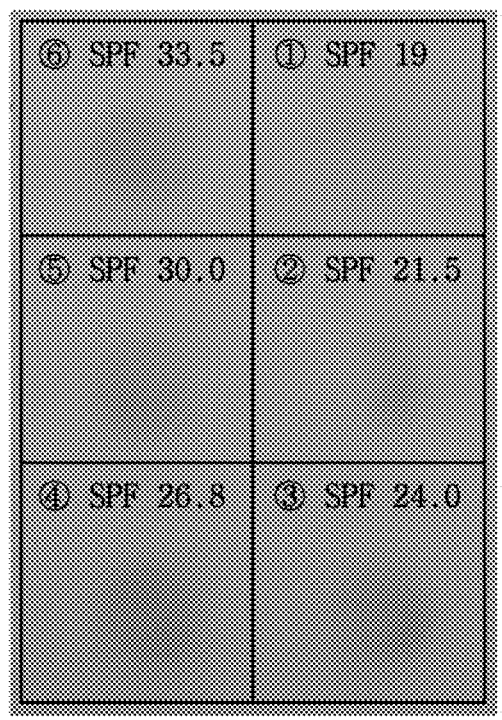
FIG. 10 is a picture showing a change in a photosensitive sheet according to light intensity of a cosmetic material measured in accordance with an embodiment of the present invention.

FIG. 10 is a picture showing reaction of a photosensitive sheet according to light intensity for predetermined reaction time.

In the embodiment of FIG. 10, data stored in advance were used, the light intensity of the picture ① corresponds to an SPF index 19, the light intensity of the picture ② corresponds to an SPF index 21.5, the light intensity of the picture ③ corresponds to an SPF index 24.0, the light intensity of the picture ④ corresponds to an SPF index 26.8, the light intensity of the picture ⑤ corresponds to an SPF index 30.0, and the light intensity of the picture ⑥ corresponds to an SPF index 33.5.

In the embodiment of FIG. 10, the reaction region of the photosensitive sheet was shown as a circle and the light intensity when the circle was shown first is the light intensity where the photosensitive sheet reacts. Referring to FIG. 10, a complete circle was shown first in the picture ④, so it can be seen that it corresponds to an SPF index 26.8.

The in-vivo test result on the third cosmetic material was SPF 28, so it can be seen that a similar result can be obtained in an embodiment of the present invention.

INDUSTRIAL APPLICABILITY

A system and method for measuring ultraviolet ray protection of a cosmetic material that can obtain a result similar to an in-vivo test by applying a wavelength of an erythema reaction band of an actual skin can be provided.

The invention claimed is:

1. A system for measuring ultraviolet ray protection ability of a cosmetic material, the system comprising:
   a light source for emitting light including ultraviolet bands;
   a transparent plate through which the light emitted from the light source passes and having one surface to which a cosmetic material to be tested is applied;
   a wavelength conversion film, which converts the light having passed through the transparent plate to have a predetermined intensity;
   a photosensitive sheet that receives the light having passed through the wavelength conversion film and that has a photosensitive property for light of UVA and UVB bands among the ultraviolet bands; and an ultraviolet ray protection calculator that
calculates the ultraviolet ray protection ability of the cosmetic material in accordance with reaction time at which the photosensitive sheet reacts, for predetermined light intensity, or
calculates the ultraviolet ray protection ability of the cosmetic material in accordance with reaction light intensity where the photosensitive sheet reacts, for predetermined reaction time.

2. The system according to claim 1, wherein the ultraviolet ray protection calculator calculates an ultraviolet ray protection index through the ratio of reaction time or light intensity for a photosensitive sheet of a transparent plate having a cosmetic material to be tested applied to a side, to reaction time or reaction light intensity for a photosensitive sheet of a transparent plate without a cosmetic material applied.

3. The system according to claim 1, further comprising:
a database storing one or more of reaction time information of a photosensitive sheet for predetermined light intensity corresponding to an ultraviolet ray protection index and reaction light intensity information of a photosensitive sheet for predetermined reaction time; and
an ultraviolet ray protection calculator connected to the database and calculating an ultraviolet ray protection index corresponding to reaction time or reaction light intensity for a photosensitive sheet of a cosmetic material.

4. The system according to claim 1, wherein the photosensitive sheet does not have a photosensitive property for bands of 380 nm or greater.

5. The system according to claim 1, wherein the photosensitive sheet has a photosensitive property for UVA II and UVB bands.

6. The system according to claim 1, wherein the photosensitive sheet has a photosensitive property for a UVB band.

7. A method of measuring ultraviolet ray protection of a cosmetic material, the method comprising:
a step of measuring first reaction time by irradiating light from a light source, which has predetermined light intensity including ultraviolet ray bands, to a photosensitive sheet having a photosensitive property for light of UVA and UVB bands of the ultraviolet ray bands through a wavelength conversion film that changes light of ultraviolet ray bands into predetermined sizes, or
measuring first light intensity for predetermined reaction time by irradiating light from a light source, which includes ultraviolet ray bands, to the photosensitive sheet through the wavelength conversion film;
a step of disposing a transparent plate having a cosmetic material to be tested applied on a side between the light source and the wavelength conversion film;
a step of measuring second reaction time by irradiating light from the light source, which has predetermined light intensity, to the photosensitive sheet through the transparent plate and the wavelength conversion film, or
measuring second light intensity for predetermined reaction time by irradiating light to a photosensitive sheet through the transparent plate and the wavelength conversion film; and
a step of calculating ultraviolet ray protection in accordance with the ratio of the second reaction time to the first reaction time or the ratio of the second light intensity to the first light intensity.

8. A method of measuring ultraviolet ray protection of a cosmetic material, the method comprising:
a step of measuring reaction time or light intensity by irradiating light from a light source, which includes ultraviolet ray bands, to a photosensitive sheet having a photosensitive property for light of UVA and UVB bands of the ultraviolet ray bands through a transparent plate having a cosmetic material to be tested applied on a side and a wavelength conversion film that changes light of ultraviolet ray bands into predetermined sizes; and
a step of calculating an ultraviolet ray protection index of the cosmetic material using one or more of reaction time information of a photosensitive sheet for predetermined light intensity corresponding to an ultraviolet ray protection index and reaction light intensity information of the photosensitive sheet for predetermined reaction time, in which the information is stored in advance.

* * * * *